US010772688B2

(12) United States Patent
Peine et al.

(10) Patent No.: US 10,772,688 B2
(45) Date of Patent: Sep. 15, 2020

(54) INPUT HANDLES FOR ROBOTIC SURGICAL SYSTEMS HAVING VISUAL FEEDBACK

(71) Applicant: Covidien LP, Mansfield, MA (US)

(72) Inventors: William Peine, Ashland, MA (US); Peter Vokrot, Malden, MA (US)

(73) Assignee: COVIDIEN LP, Mansfield, MA (US)

(*) Notice: Subject to any disclaimer, the term of this patent is extended or adjusted under 35 U.S.C. 154(b) by 109 days.

(21) Appl. No.: 15/768,266

(22) PCT Filed: Oct. 27, 2016

(86) PCT No.: PCT/US2016/058973
§ 371 (c)(1),
(2) Date: Apr. 13, 2018

(87) PCT Pub. No.: WO2017/075122
PCT Pub. Date: May 4, 2017

(65) Prior Publication Data
US 2018/0310997 A1 Nov. 1, 2018

Related U.S. Application Data

(60) Provisional application No. 62/248,548, filed on Oct. 30, 2015.

(51) Int. Cl.
A61B 17/00 (2006.01)
A61B 17/32 (2006.01)
(Continued)

(52) U.S. Cl.
CPC .............. *A61B 34/25* (2016.02); *A61B 17/00* (2013.01); *A61B 34/00* (2016.02); *A61B 34/37* (2016.02);
(Continued)

(58) Field of Classification Search
CPC ......... A61B 19/00; A61B 18/18; A61B 90/10; A61B 34/30; A61B 18/1445; A61B 2017/00477; A61B 2018/1226; A61B 90/03; A61B 2017/00734; A61B 18/1442; A61B 34/37; A61B 34/74; A61B 34/77; A61B 90/90; A61B 17/320092; A61B 34/76; A61B 18/12; A61B 2018/00303; A61B 2017/320094; A61B 2017/320093; A61B 2017/320095; A61B 34/70; A61B 17/00491; A61B 34/71;
(Continued)

(56) References Cited

U.S. PATENT DOCUMENTS 8,828,023 B2 9/2014 Neff et al.
2007/0142825 A1 6/2007 Prisco et al.
(Continued)

OTHER PUBLICATIONS

Partial Supplementary European Search Report corresponding to counterpart Patent Application EP 16860740.6 dated May 22, 2019.
(Continued)

*Primary Examiner* — Jon Eric C Morales

(57) ABSTRACT

An input device for a robotic surgical system includes a body, a light source, and control interfaces. The body is configured to couple to a user interface. The control interfaces are each associated with a function of the robot system. The light source is configured to selectively illuminate each of the control interfaces independent of one another.

11 Claims, 3 Drawing Sheets

(51) Int. Cl.
  *A61B 18/18* (2006.01)
  *A61B 34/00* (2016.01)
  *A61B 34/37* (2016.01)
  *A61B 90/00* (2016.01)
  *A61B 90/90* (2016.01)

(52) U.S. Cl.
  CPC .............. *A61B 34/74* (2016.02); *A61B 90/37* (2016.02); *A61B 90/90* (2016.02); *A61B 2017/00022* (2013.01); *A61B 2017/00115* (2013.01); *A61B 2017/00119* (2013.01); *A61B 2017/00128* (2013.01); *A61B 2017/00216* (2013.01); *A61B 2017/00907* (2013.01); *A61B 2034/252* (2016.02); *A61B 2090/0804* (2016.02); *A61B 2090/376* (2016.02); *A61B 2090/378* (2016.02)

(58) Field of Classification Search
  CPC .... A61B 2017/00207; A61B 2034/742; A61B 2090/3784; A61B 2034/741; A61B 2017/00867; A61B 2017/00247; A61B 2017/003; A61B 2017/00084; A61B 2017/00398; A61B 2017/0065; A61B 17/3478
  USPC .................................................. 606/33, 130
  See application file for complete search history.

(56) References Cited

U.S. PATENT DOCUMENTS

| | | |
|---|---|---|
| 2011/0178532 A1 | 7/2011 | Amiri et al. |
| 2011/0224689 A1 | 9/2011 | Larkin et al. |
| 2014/0005682 A1 | 1/2014 | Worrell et al. |
| 2014/0194897 A1 | 7/2014 | Kirschenman et al. |
| 2015/0173837 A1 | 6/2015 | Barnett |

OTHER PUBLICATIONS

International Search Report dated Feb. 3, 2017 in PCT/2016/058973.

INPUT HANDLES FOR ROBOTIC SURGICAL SYSTEMS HAVING VISUAL FEEDBACK

CROSS-REFERENCE TO RELATED APPLICATIONS

The present application is a U.S. National Stage filed under 35 U.S.C. § 371(a) of International Patent Application Serial No. PCT/US2016/058973, filed on Oct. 27, 2016, which claims the benefit of and priority of U.S. Provisional Patent Application Ser. No. 62/248,548, filed on Oct. 30, 2015, the entire content of each of which being incorporated herein by reference.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes a handle or gimbal that is moveable by the surgeon to control the robotic system.

There is a need for improved feedback systems for providing visual feedback to a surgeon interfacing with the user interface during a surgical procedure.

SUMMARY

The present disclosure relates generally to input devices for providing visual feedback during a surgical procedure to a clinician operating a robotic surgical system. The input devices are mounted to an input shaft of a gimbal of a user interface of a robotic surgical system. As a clinician interfaces with the user interface, the input device provides light or visual feedback to the clinician.

In an aspect of the present disclosure a robotic surgical device includes a plurality of robotic arms, a surgical instrument detection system, a user input device, and a processing unit. Each robotic arm is configured to manipulate in at least three dimensions a surgical instrument attached thereto. The surgical instrument detection system is configured to identify a surgical instrument of each robotic arm. The user input device is manipulatable in at least three dimensions and has a first illuminable feature that is visible to a user. The processing unit is configured to selectively associate the user input device with one of the robotic arms, to manipulate a surgical instrument attached to the robotic arm based on a corresponding detected manipulation of the user input device, and to selectively illuminate the first illuminable feature of the user input device based on a state of the surgical instrument of the respective robotic arm associated with the user input device. The surgical instrument may be selectively removable from the respective robotic arm.

In some aspects, the first illuminable feature of the user input device is selectively illuminated based on a state of the respective robot arm. Selectively illuminating the first illuminable feature includes illuminating the first illuminable feature in a plurality of illumination pattern or a plurality of illumination colors including, but not limited to, steady, short blinking, long blinking, varied bling, alternating color, or a steady color. The plurality of illumination patterns or colors may be selected based on a type of surgical instrument attached to the respective arm.

In particular aspects, selectively illuminating the first illuminable feature includes illuminating the first illuminable feature in a plurality of illumination patterns based on a state of the surgical instrument attached to the respective arm and illuminating the first illuminable feature in a plurality of illumination colors based on a type of surgical instrument attached to the respective arm. Alternatively, selectively illuminating the first illuminable feature include illuminating the first illuminable feature in a plurality of illumination colors based on a state of the surgical instrument attached to the respective arm and illuminating the first illuminable feature based on a type of a surgical instrument attached to the respective arm.

In certain aspects, the user input device includes a second illuminable feature that is visible to a user. The first illuminable feature may be illuminated in response to a type of the surgical instrument attached to the respective arm and the second illuminable feature may be illuminated in response to a state of the surgical instrument attached to the respective arm.

In another aspect of the present disclosure, an input device for a robotic surgical system includes a body, at least one light source, and a plurality of control interfaces. The body is configured to couple to a user interface. Each of the plurality of control interfaces is associated with a function of a robot system. The at least one light source is configured to selectively illuminate each of the plurality of control interfaces independent of one another.

In aspects, the at least one light source includes a first light source and a second light source that is disposed within the body. The first light source may be configured to illuminate a respective one of the plurality of control interfaces with light having a first wavelength and the second light source may be configured to illuminate the respective one of the plurality of control interfaces with light having a second wavelength that is different from the first wavelength.

In some aspects, the at least one light source may be configured to illuminate the body. The body may be constructed at least in part of a material that is translucent.

In certain aspects, the plurality of control interfaces includes a plurality of petals that are disposed radially about a first end of the body. The at least one light source may include a light source that is disposed in each of the plurality of petals. The at least one light source may include a first light source and a second light source disposed in a respective one of the plurality of petals. The first light source may be configured to illuminate the respective one of the plurality of petals with light having a first wavelength and the second light source may be configured to illuminate the respective one of the plurality of petals with light having a second wavelength different from the first wavelength.

In particular aspects, the at least one light source is configured to vary properties of light illuminating the plurality of control interfaces in response to a condition or state of the robotic surgical system. The properties of light may be color, intensity, pattern, or combinations thereof. The at least one light source may be configured to illuminate a respective on of the plurality of control interfaces when a function of the robotic surgical system associated with the respective one of the plurality of control interfaces is activatable. The at least on light source may generate light with a light emitting diode.

In another aspect of the present disclosure, a robotic surgical system includes a robot system, a processing unit, and a user interface. The robot system is configured to perform surgery on a patient. The processing unit is in communication with the robot system to send control signals to the robot system and to receive feedback signals from the robot system. The user interface is in communication with the processing unit to generate the control signals in response to input from a user and to provide feedback to the user in response to the feedback signals. The user interface includes a control arm and an input device that is coupled to the control arm. The input device includes a body, at least one light source, and a plurality of control interfaces. The body is coupled to the control arm. The plurality of control interfaces are each associated with at least one function of the robot system. The at least one light source is configured to selectively illuminate the plurality of control interfaces in response to the feedback signals.

In aspects, the at least one light source is configured to illuminate a respective one of the plurality of control interfaces of the input device in response to the feedback signals. The at least one light source may be configured to illuminate the body of the input device in response to the feedback signals. The feedback signals may be indicative of a state of the robot system. The at least one light source is configured to illuminate the body or a respective one of the plurality of control interfaces in response to a state of the robotic surgical system.

In another aspect of the present disclosure, a method of controlling a robotic surgical system with visual feedback includes manipulating an input device coupled to a user interface of the robotic surgical system to manipulate a tool of the robotic surgical system, receiving a feedback signal from a processing unit of the robotic surgical system with a feedback controller, and activating a light source in response to the feedback signal to illuminate portions of the input device to provide an indication of a condition of the robotic surgical system. The feedback control is in communication with the light source disposed within the input device.

In aspects, activating the light source in response to the feedback signal includes illuminating a first control interface of the input device in response to a first condition of the robotic surgical system and illuminating a second control interface of the input device in response to a second condition of the robotic surgical system. The first control interface may be different from the second control interface. Activating the light source in response to the feedback signal may include varying a property of light generated by the light source. The property of light may include, but is not limited to, color, intensity, pattern, or combinations thereof.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
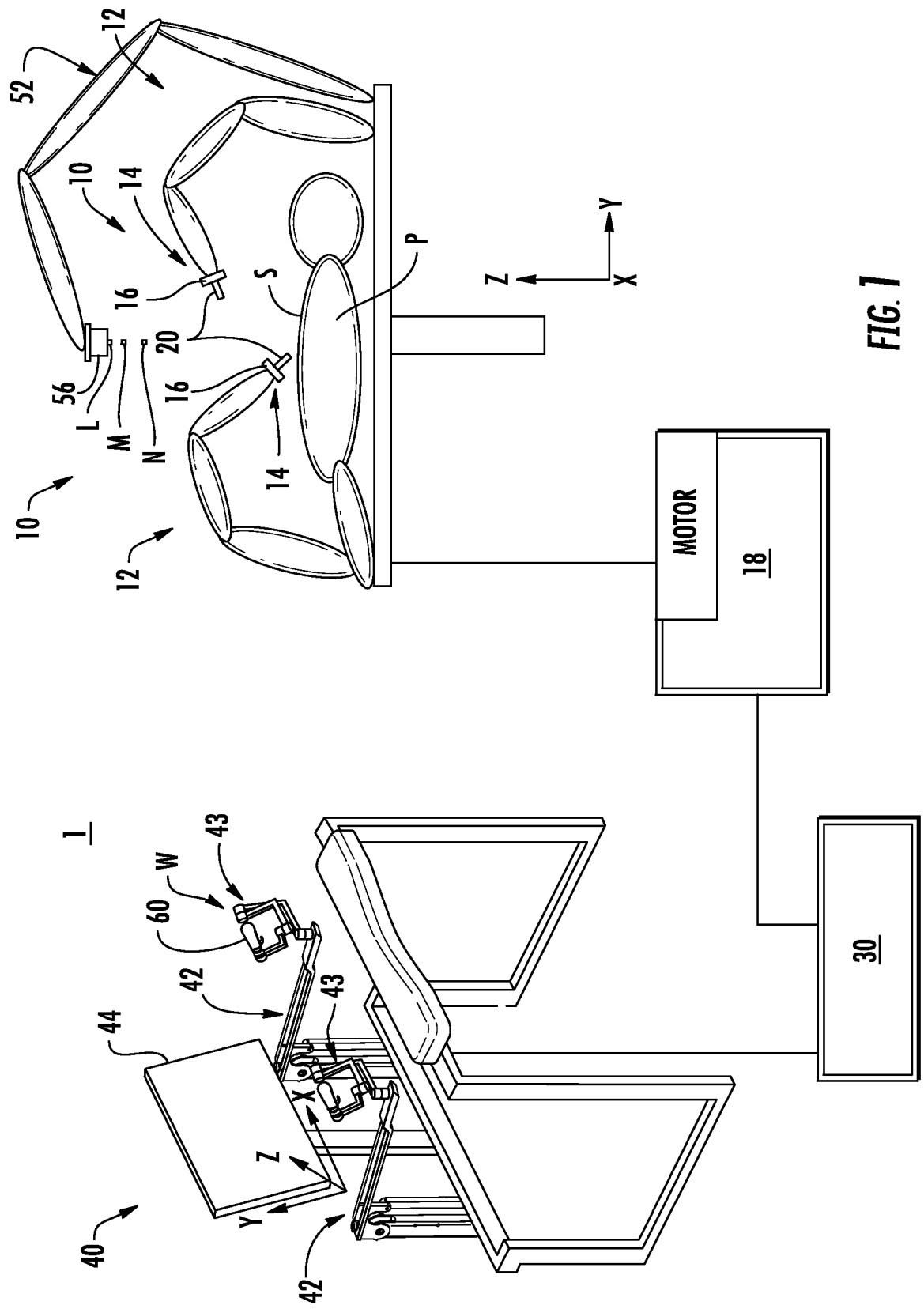
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure relates generally to input devices for providing visual feedback during a surgical procedure to a clinician operating a robotic surgical system. The input devices are mounted to an input shaft of a gimbal of a user interface of a robotic surgical system. As a clinician interfaces with the user interface, the input device provides light or visual feedback to the clinician.

Referring to FIG. 1, a robotic surgical system 1 is shown generally as a robot system 10, a processing unit 30, and a user interface 40. The robot system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the arms 12 may include an imaging device 16 for imaging a surgical site "S". The ends 14 of the arms 12 may include a tool detection system that identifies a type of surgical instrument supported or attached to the end 14 of the arm 12. The user interface 40 is in communication with robot base 18 through the processing unit 30.

The user interface 40 includes a display device 44 which is configured to display images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates images (e.g., three-dimensional images) of the surgical site "S" in real-time from the imaging data and transmits the images to the display device 44 for display.

Figure 2:
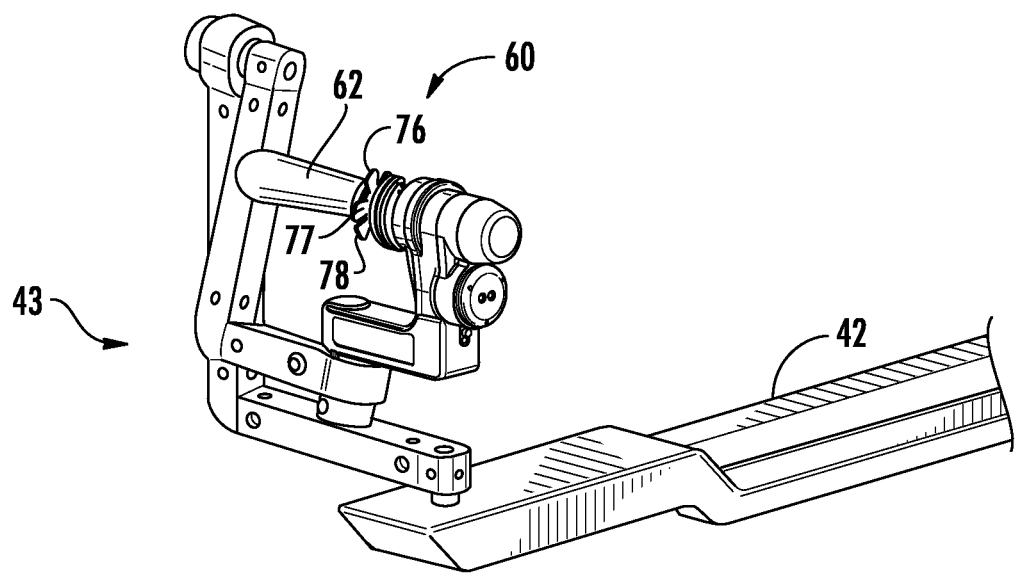
FIG. 2 is an enlarged perspective view of a user device attached to a gimbal of the user interface of FIG. 1.

The user interface 40 also includes input handles or gimbals 43 which allow a clinician to manipulate the robot system 10 (e.g., move the arms 12, the ends 14 of the arms 12, and/or the tools 20). Each of the gimbals 43 is supported at the end of a control arm 42 and is in communication with the processing unit 30 to transmit control signals thereto and to receive feedback signals therefrom. With additional reference to FIG. 2, each of the gimbals 43 includes control interfaces or input devices 60 which allow the surgeon to manipulate (e.g., clamp, grasp, fire, open, close, rotate, thrust, slice, etc.) the tools 20 supported at the ends 14 of the arms 12.

Each of the gimbals 43 is moveable to move the ends 14 of the arms 12 within a surgical site "S". The images on the display device 44 are orientated such that the movements of the gimbals 43 move the ends 14 of the arms 12 as viewed on the display device 44. It will be appreciated that the orientation of the images on the display device may be mirrored or rotated relative to view from above the patient "P". In addition, it will be appreciated that the size of the images on the display device 44 may be scaled to be larger or smaller than the actual structures of the surgical site "S" permitting the surgeon to have a better view of structures within the surgical site "S". As the gimbal 43 is moved, the tools 20 are moved within the surgical site "S". Movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 3:
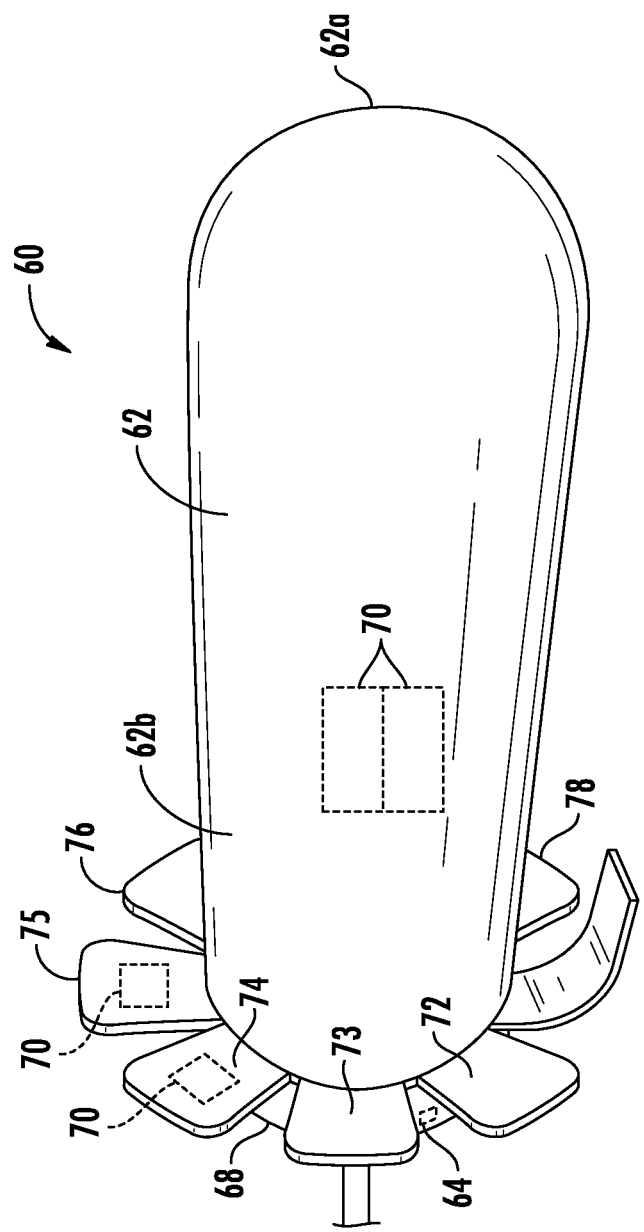
FIG. 3 is an enlarged perspective view of the input device of FIG. 2.

Referring now to FIG. 3, an input device 60 provided in accordance with the present disclosure includes a body 62 and a plurality of control interfaces or petals 72-78. The body 62 may be compressible to control a function of the tool 20 (e.g., movement of jaws towards one another). Each of the petals 72-78 may be associated with a function of the tool 20, imaging device 16, 56, or of the user interface 40. For example, one petal (e.g., petal 75) may clutch movement of the user interface 40 from movement of the tool 20, another petal (e.g., petal 72) may zoom an imaging device 16, 56 in or out, another petal (e.g., petal 73) may control delivery of electrosurgical energy from the tool 20, and another petal (e.g., petal 76) may actuate a knife of the tool 20.

The input device 60 includes one or more illuminable features or light sources 70. The light sources 70 may be disposed within the body 62 or within the petals 72-78. The light sources 70 are configured to selectively illuminate portions of the body 62 and/or the petals 72-78 to provide visual feedback to a clinician interfacing with the input device 60. The light sources 70 may be LED lights that are selectively activated by a feedback controller 64 that is in communication with the processing unit 30 (FIG. 1). Each light source 70 may be associated with one or more portions of the body 62 and/or one or more of the petals 72-78. The light sources 70 may illuminate portions of the body 62 and/or petals 72-78 with light of varying wavelengths or colors. Additionally or alternatively, the feedback controller 64 may vary the intensity and/or pattern of the light provided by the light sources 70. The body 62 of the input device 60 may be fabricated from transparent or translucent materials, e.g., polycarbonate, which allow for visual indications produce by each light source 70 to be visible through the body 62.

It is contemplated that the lighting of the petals 72-78 and/or portions of the body 62 may be configured based on the type of tool 20 (e.g., a stapler, an endoscope, a grasper, an electrosurgical tool, etc.) attached to the end 14 of an arm 12 that is associated with the respective input device 60.

The visual feedback can be indicative to the state or condition of the robotic surgical system 1. In response to a feedback signal from the processing unit 30, the feedback controller 64 activates visual feedback of the input device 60. The feedback controller 64 may uniquely activate the light sources 70 for each condition of the robotic surgical system 1. The feedback controller 64 may vary the color, wavelength, intensity, or pattern of the light sources 70 for each condition of the robotic surgical system 1. For example, the feedback controller 64 may activate a light source 70 to illuminate petal 75 with a flashing light having an interval of 0.25 seconds as the input device 60 approaches a limit of movement and then activate the light source 70 to illuminate the petal 75 with a steady light when the input device 60 reaches a limit of movement indicating that the input device 60 must be clutched for continued movement of a tool 20. Additionally or alternatively, the feedback controller 64 may activate a light source 70 to illuminate petal 75 with a yellow light as the input device 60 approaches a limit of movement and the activates the light source 70 to illuminate the petal 75 with a red light when the input device 60 reaches the limit of movement indicating that the input device must be clutched for continued movement of the tool 20.

The body 62 or petals 72-78 may also provide visual feedback with respect to the mode of the tool 20. For example, the feedback controller 64 may illuminate petal 73 when the tool 20 is in a cauterization mode and may illuminate petal 77 (FIG. 2) when the tool 20 is in a staple firing mode. It is contemplated that the feedback controller 64 may be customizable for a clinician. Additionally or alternatively, the feedback controller 64 may vary wavelength or color of light illuminating the entire body 62 or a portion of the body 62 (e.g., a proximal portion 62a or a distal portion 62b) to indicate a mode of the tool 20 or the robotic surgical system 1. For example, the body 62 may be illuminated with green light when the input device 60 is operating normally, may be illuminated with blue light when the input device 60 is being held for the completion of a function of the tool 20 (e.g., application of electrosurgical energy or firing of staples), and may be illuminated with red light when there is an error in a condition of the robotic surgical system 1.

The condition of the robotic surgical system 1 may include, but is not limited to, the tool 20 reaching an end of range, the input device 60 being clutched in or out, the need to clutch an input device 60, the input device 60 being switched to a camera control state, a state or mode change of the tool 20 (e.g., cauterization mode, staple firing mode), the presence of a message on the display 44, a tool 20 being changed, collision avoidance (e.g., collision of tools 20), a tool 20 approaching a target, a tool 20 contacting a structure, vibration of a tool 20, a measurement of a grasping force of a tool 20. It is contemplated that the condition of the robotic surgical system 1 may include the status of the patient "P" (e.g., vital signs of the patient "P") and/or the status of the clinician (e.g., the robotic surgical system 1 may include a clinician attention monitor (not shown) that provides feedback of the direction of the clinician's gaze). The feedback controller 64 may activate visual, audible, vibratory or haptic, and force feedback of the input device 60.

The feedback controller 64 may be in communication with an intensity dial 68 that allows a clinician to select an intensity of light of the light sources 70. As shown, the intensity dial 68 is a rotary switch positioned on the input device 60; however, it is contemplated that the intensity dial 68 may be positioned on the input device 60 or may be accessible through the display 44 of the user interface (e.g., on a screen menu). It is also contemplated that the intensity dial 68 may be a toggle switch, a slide switch, a jumper switch, or a button switch. The intensity dial 68 may include high, medium, and low intensity settings for the light sources 70.

The wireless connections detailed herein (e.g., between feedback controller 64 and the processing unit 30) may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An input device for a robotic surgical system, the input device comprising:
   a body configured to couple to a user interface;
   at least one light source; and
   a plurality of control interfaces each associated with at least one function of the robotic surgical system, the at least one light source configured to selectively illuminate each of the plurality of control interfaces independent of one another in response to a state of the robotic surgical system, wherein the plurality of control interfaces includes a plurality of petals disposed radially about a first end of the body.

2. The input device according to claim 1, wherein the at least one light source includes a first light source and a second light source disposed within the body.

3. The input device according to claim 2, wherein the first light source is configured to illuminate a respective one of the plurality of control interfaces with light having a first wavelength and the second light source is configured to illuminate the respective one of the plurality of control interfaces with light having a second wavelength different from the first wave length.

4. The input device according to claim 1, wherein the at least one light source is configured to illuminate the body.

5. The input device according to claim 1, wherein at least a portion of the body is constructed of a material that is translucent.

6. The input device according to claim 1, wherein the at least one light source includes a light source disposed in each of the plurality of petals.

7. The input device according to claim 1, wherein the at least one light source includes a first light source and a second light source disposed in a respective one of the plurality of petals.

8. The input device according to claim 7, wherein the first light source is configured to illuminate the respective one of the plurality of petals with light having a first wavelength and the second light source is configured to illuminate the respective one of the plurality of petals with light having a second wavelength different from the first wavelength.

9. The input device according to claim 1, wherein the at least one light source is configured to vary properties of light illuminating the plurality of control interfaces in response to a condition or state of the robotic surgical system, the properties of light selected from the group consisting of color, intensity, pattern, and combinations thereof.

10. The input device according to claim 1, wherein the at least one light source is configured to illuminate a respective one of the plurality of control interfaces when a function of the robotic surgical system associated with the respective one of the plurality of control interfaces is activatable.

11. The input device according to claim 1, wherein the at least one light source generates light with a light emitting diode.

* * * * *